United States Patent [19]

Arai et al.

[11] Patent Number: 4,996,041
[45] Date of Patent: Feb. 26, 1991

[54] METHOD FOR INTRODUCING OXYGEN-17 INTO TISSUE FOR IMAGING IN A MAGNETIC RESONANCE IMAGING SYSTEM

[76] Inventors: Toshiyuki Arai, 26-46 Nishifukunokawa-cho, Okazaki, Sakyo-ku, Kyoto 606, Japan; Pradeep M. Gupte, 3 Larissa Ct., Tallman, Monsey, N.Y. 10952; Sigmund E. Lasker, 531 Main St., New York, N.Y. 10044

[21] Appl. No.: 234,339

[22] Filed: Aug. 19, 1988

[51] Int. Cl.$^5$ ................ G01N 24/00; A61B 6/00
[52] U.S. Cl. ........................ 424/9; 128/654; 128/653
[58] Field of Search ............. 424/9; 128/653, 654

[56] References Cited
U.S. PATENT DOCUMENTS 4,586,511  5/1986  Clark, Jr. ............... 436/173
4,775,522  10/1988  Clark, Jr. ............... 424/9

*Primary Examiner*—Stanley J. Friedman
*Assistant Examiner*—Raymond J. Henley, III
*Attorney, Agent, or Firm*—Lieberman, Rudolph & Nowak

[57] ABSTRACT

A diagnostic imaging agent is provided for use in conjunction with a magnetic resonance imaging system for the imaging of spacial oxygen distribution in tissue. The imaging agent is comprised of a complex of oxygen-17, a biologically acceptable liquid carrier, such as a perfluorinated compound, and an emulsifying agent, and wherein the agent has an average particle size of less than about 0.6 microns, and an ionic composition essentially equal to that of blood. Useful information can be obtained, and in certain instances, therapy administered, by a non-envasive imaging technique relative to tissue perfusion by $^{19}$F-NMR (imaging of $^{19}$F) and oxygen utilization by $^1$H-NMR (imaging of H$_2$$^{17}$O as a metabolite).

13 Claims, No Drawings

METHOD FOR INTRODUCING OXYGEN-17 INTO TISSUE FOR IMAGING IN A MAGNETIC RESONANCE IMAGING SYSTEM

FIELD OF THE INVENTION

This invention relates in general to a method for introducing oxygen-17 ($^{17}O$) into tissues for imaging in an magnetic resonance imaging system. In one aspect, this invention is directed to a non-invasive method useful for obtaining information about tissue perfusion by $^{19}F$-NMR (imaging of $^{19}F$) and oxygen utilization by $^{1}H$-NMR (imaging of $H_2^{17}O$ as a metabolite). In another aspect this invention is directed to a diagnostic imaging agent comprised of a complex of oxygen-17 and a biologically acceptable fluid. In a further aspect, this invention is directed to an emulsified complex of a perfluorinated compound and oxygen-17 as well as to a method for its preparation.

BACKGROUND OF THE INVENTION

Magnetic resonance imaging systems rely on the tendency of atomic nuclei possessing magnetic moments to align their spins with an external magnetic field Only nuclei with odd numbers of nucleons have a magnetic moment, so only these nuclei can be detected and imaged. Hydrogen has one nucleon, a proton, in its nucleus and is the primary nucleus imaged at this time in medical practice.

The most common isotope of oxygen, oxygen-16, has an even number of nucleons and hence, cannot be imaged in a magnetic imaging system. Oxygen-15 is unstable (radioactive) and is used in other imaging techniques which subject the host to a radiation dose. Oxygen-17 is stable and meets the odd nucleon number critera necessary for magnetic resonance imaging, but it is extremely rare and hence has not been utilized since relatively large quantities would be needed.

Prior to the present invention, the oxygen-17 isotope had only been utilized for diagnostic purposes by administering the isotope into a warm blooded animal in the form of water. By following the distribution of water in the body using magnetic resonance imaging it was possible to trace the location of the oxygen-17 isotope.

Some of the earlier investigations on NMR study of the protein transfer in water as reported by S. Meiboom, *J. Chem. Phys.*, 39, 375, 1961, showed that at neutral pH, protein transverse relaxation time ($T_2$) is significantly shorter than longitudinal relaxation time ($T_1$). The author suggested that this difference is due to the naturally occurring $H_2^{17}O$ isotope (0.037 at.) in the $H_2^{16}O$ and at a neutral pH this effect is greater due to scalar coupling interactions between the guadrupole $^{17}O$ and protons. Meiboom further demonstrated that at any pH above or below the neutral pH the resident lifetime of the protons on 170 (spin=5/2) is too short to produce any enhancement of relaxation. In contrast to $T_2$, $T_1$ was not affected by enrichment or pH.

In work by Hopkins et al *Mag. Reson. Med.* 4, 399, 1987, there is reported the enrichment effects of $H_2^{17}O$ on protein solutions and living tissues which is in agreement with Meiboom's protein exchange rate studies.

In the Research Resources Reporter, Aug., 1988, it is disclosed on page 12 that fluorine was used in conjunction with magnetic resonance imaging (MRI) to obtain information about blood flow. It was indicated therein that accurate information could be obtained by the study of several nuclei simultaneously and blood flow could be measured on a real-time basis. Dr. J.S. Leigh, one of the coauthors, disclosed that by combining MRI and magnetic resonance spectroscopy (MRS), one could obtain an image of the inside of a person and obtain a very complete biochemical analysis of what is there.

However, as previously indicated, administration of the oxygen-17 isotope had only been effected by the use of water containing the isotope. Accordingly, one or more of the following objects will be achieved by the practice of this invention. It is an object of this invention to provide a method for introducing oxygen-17 into tissues for imaging in a magnetic imaging system. Another object of this invention is to provide a method for detecting localized metabolic activity under physiological conditions by monitoring the in vivo production of $H_2^{17}O$ metabolite in tissue utilizing oxygen-17, promoted proton $T_2$ relaxation enhancement. A further object of the present invention is to provide a novel complex of the oxygen-17 isotope and a biologically acceptable liquid emulsion carrier which can be administered to a warm blooded animal to detect localized metabolic activity. A still further object is to provide a novel complex of the oxygen-17 isomer and a perfluorinated compound. Another object of this invention is to provide a complex of the oxygen-17 isomer and perfluorotributylamine. Another object of this invention is to provide a method for preparing the novel complex of this invention. A still further object of the invention is to provide a method for introducing the complex of the oxygen-17 isomer into a warm blooded animal for the detection of localized metabolic activity. Another object is to obtain information about tissue perfusion by imaging fluorine-19 and oxygen utilization by imaging $H_2^{17}O$ as a metabolite. These and other objects will readily become apparent to those skilled in the art in the light of the teachings herein set forth.

SUMMARY OF THE INVENTION

In its broad aspect, the present invention relates to a novel complex of the oxygen-17 isotope and a biologically acceptable liquid carrier, a method for its preparation and a method for infusing the complex into tissues for imaging in a magnetic imaging system.

DETAILED DESCRIPTION OF THE INVENTION

Prior to the present invention much interest had been expressed in the use of perfluorohydrocarbons as oxygen carrying blood substitutes and their efficiency in delivering oxygen to a target organ. Oxygen is highly soluble in liquid perfluoro-chemicals. In contrast, normal saline or blood plasma dissolves about 3 percent oxygen by volume, whole blood about 20 percent, whereas perfluorochemicals can dissolve up to 40 percent and more.

However, even though the fluorochemicals have the ability to absorb large quantities of oxygen, the intravenous injection of perfluorochemicals can be highly toxic since they are immiscible with blood and can therefore produce emboli. Thus, while it was known in the literature that perfluorochemicals were excellent carriers of oxygen, prior to the present invention they had never been complexed with the oxygen-17 isotope and utilized for imaging both tissue perfusion and spacial oxygen distribution.

As hereinbefore indicated the present invention relates to a novel diagnostic imaging agent containing oxygen-17, a method for its preparation and is use in imaging fluorine-19 perfusion and oxygen-17 metabolism. The method is useful for the direct detection of fluorine-19 by $^{19}$F-NMR and the indirect detection of oxygen-17 in $H_2^{17}O$, the metabolite of the new mixture by $^1$H-NMR. The distribution of the complex and its metabolite can be imaged simultaneously or alternatively in clinical magnetic resonance systems.

The diagnostic imaging agent is comprised of a complex of oxygen-17, a biologically acceptable liquid carrier and a biologically acceptable emulsifying agent, and wherein the complex has an ionic composition essentially equal to that of blood, and an average particle size of less than about 0.6 microns.

Oxygen-17 is a commercially available isotope and while not produced in large quantities can be obtained from several sources.

In practice, it has been found that a perfluorinated compound is preferred as the biologically acceptable carrier, although it is possible to use other liquids including blood or blood plasma. The perfluorinated compounds, however, have the ability, as previously described, to absorb large amounts of oxygen.

Illustrative compounds include but are not limited to, perfluorinated compounds such as perfluorotributylamine, perfluorobutyltetrahydrofuran, perfluoro-n-octane, perfluoropolyether, perfluorodecalin, perfluoromethyldecalin, perfluororcyclohexyldiethylamine, perfluoro-isopentylpyran, perfluorodibutylmethylamine, and the like.

The emulsifying agent or surfactant can be selected from a wide variety of commercially available products. The particular agent chosen will, of course, be one which is non-toxic, biologically acceptable, compatable with both the oxygen-17 and the perfluorinated compound, and have no adverse affects on the body. It has been observed that the known family of polyoxyethyenepolyoxypropylene copolymers not only emulsify the organic phase, but can also serve as a plasma expander to reproduce the oncotic pressure normally provided by blood proteins. These polyols are nontoxic at low concentrations and unlike many ionic and non-ionic surfactants, they do not cause hemolysis of erythrocytes. A particularly preferred surfactant which can be used as the emulsifying agent in the present invention is Pluronic F-68 which is available from Asaki Denka Inc., Tokyo, Japan. This copolymer has a mean molecular weight of about 8350 and is a non-ionic surfactant and detergent.

In practice, the diagnostic agent of the present invention contains about 5 to about 50, and more preferably from about 15 to about 30 percent by weight of the perfluorinated compound and from about 1 to about 20, and more preferably from about 2.5 to about 10 percent by weight of the surfactant in an aqueous solution with an ionic composition resembling that of blood.

Preparation of the complex of the oxygen-17, perfluorinated compound and the emulsifying agent is effected by the steps of:

(1) deoxygenating an emulsion of:

(a) a biologically acceptable liquid, perfluorinated compound having an average particle size of less than about 0.6 microns, and (b) a biologically acceptable emulsifying agent, by at least one freeze-thaw cycle followed by sparging said emulsion with an inert oxygen-free gas; (2) introducing oxygen-17 into the emulsion, and (3) thereafter recovering the diagnostic imaging agent.

In some instances it may be necessary to subject the liquid to multiple freeze-thaw cycles in order to assure that removal of all oxygen-16 is completed before introducing the oxygen-17 isotope. Under some circumstances, it might also be desirable to conduct the deoxygenation step under reduced pressure.

Administration of the diagnostic agent is preferably carried out by intravenous perfusion. A wide variety of methods and instrumentation can be 1 employed to introduce the agent into the body of the subject being examined. One preferred method is to use a catheter so that the agent can be directed to a particular site in the body and greater control can be obtained of the amount introduced to provide the desired imaging. By using a catheter it is also possible to administer therapeutic agents after or during the imaging procedure.

Since the oxygen-17 is complexed with a perfluorinated compound, it is theoretically possible to infuse up to about 30 percent of the total blood volume in a subject with the complex, without adverse effects.

The amount actually employed to achieve the desired imaging, will, of course, depend, in part, on the degree of enhancement of oxygen-17 in the gas. While a 99 percent enrichment is desired, oxygen-17, which is formed in the manufacture of oxygen -18, is usually obtained in 70 percent enrichment.

In general, the ratio of oxygen-17 to the perfluorinated compound and emulsifying agent, will usually be at least about 1:5. Thus, in a preferred aspect, 100 ml of the enriched gas is complexed with 100 ml of the perfluorinated compound and emulsifying agent. The complex will be employed in an effective amount necessary to provide the desired imaging, and this can vary from a few milliters to ten milliters or more.

A further advantage of the present invention is that the imaging agent can be detected using commercially available magnetic resonance equipment with little or no modification. Commercially available MRI units can be characterized by the magnetic field strength used, with a field strength of 2.0 Tesla as the current maximum and 0.2 Tesla the current minimum. For a given field strength, each nucleus has a characteristic frequency. For instance, at a field strength of 1.0 Tesla, the resonance frequency for hydrogen is 42.57 MHz; for phosphorus-31, 17.24; and for sodium-23, 11.26 MHz. Higher field strengths may be desirable for imaging nuclei other than hydrogen. Thus, for imaging the oxygen-17 metabolite and fluorine-19, existing equipment can be used. Moreover, the imaging of the elements can be conducted simultaneously or sequentially.

The method of the present invention makes possible the non-invasive and visual estimation of the spacial oxygen distribution in brain and other important organs such as the heart, liver, kidney and the like, under clinical magnetic resonance systems.

The visual imaging of the spacial oxygen distribution in organs gives information about the oxygen delivery to tissues and the utilization of oxygen in such tissue, which is extremely useful to estimate the pathophysiological status of patients in clinical practice.

The imaging agent and the method of use as described previously, are characterized by several other desirable features Since all of the oxygen-17 employed can be complexed with the fluorinated compound prior to use, complete control can be maintained over the amount of the isotope used and little if any is lost as would be the case if administered by inhalation. Moreover, the diagnostic agent of this invention is easily produced and the resulting complex can be administered intravenously in the same manner as a venous transfusion, and hence is essentially a non-invasive method. Moreover, when used in conjunction with a catheter, the complex can be delivered directly to the tissue under study.

Accordingly, in clinical MRI systems, the novel diagnostic imaging agent of the invention can give information about tissue perfusion by fluorine-19 and oxygen utilization by $^1$H-NMR.

The NMR imaging work was done on a General Electric 1.5 T Signa Imaging system ( 1H resonant frequency 63.9 MHz). At 1.5T, in vitro $T_1$ determination of 35.9 at . % enriched Oxygen-17 water gave a value of 1910±68 msec. This supports the earlier observation that $^{17}$O is a weak protonrelaxing agent which therefore must be used at relatively high concentrations. In contrast to $T_1$,l the measured $T_2$ value of the enriched water ( 35.9 at. %) was 10.6±0.4 msec demonstrating $^{17}$O promoted proton $T_2$ relaxation enhancement. In vitro $T_1$ and $T_2$ values of PFC (FC emulsions) were determined to be 2064±14 msec and about 800 msec respectively. The $T_2$ value of the PFC-17$O_2$ complex determined 4 hours. After oxygenation of the PFC with 17$O_2$ gave a value of about 190 msec.

The following example is illustrative of the invention.

EXAMPLE 1

The complex employed was prepared by deoxygenation of natural oxygen (oxygen-16) from a mixture of perfluorotributylamine (PFC) and a polyoxyethylene-polyoxypropylene emulsifying agent obtained from the Green Cross Corporation of Osaka, Japan. The mixture was sparged with nitrogen and warmed to remove the oxygen-16. Thereafter, the mixture was contacted with an equal volume of 70% oxygen-17 gas and mixed well to insure absorption of the gas. The resulting mixture consisted of 100 ml of complex and was kept under cooling conditions)

A dog (body weight 5 kg) was anesthetized with pentabarbital (30 mg/kg). A cannula was inserted into a femoral vein to an interior vena cava for saline infusion (10 ml/kg/hr) and later infusion of the(oxygen-17-PFC complex.

The dog was fixed on the platform and positioned in the knee coil under the GE 1.5 Tesla Sigma Imaging system (1H resonant frequency, 63.9 Mhz). A control image was obtained with the infusion system in place. The dog brain was scanned before (control), during, and after infusion of the complex and 5 mm thick axial images at different locations (multislice) of the brain tissue were obtained. The images were reconstructed using 2 DFT of two exitations of 256 data lines and magnitude reconstruction.

After getting the control image of the brain, the complex was infused through the cannula at a constant rate (100 ml/8 min). During and after the infusion, the dog brain was scanned at different locations, and several sets of images were obtained over a two hour period.

Compared to the control image, the $T_2$-weighted images exhibited considerable decrease (32–40%) in proton intensity. This effect was not transitory but persisted for at least 2 hours, and thought to be due to the paramagnetic effect of oxygen-17 derived from $H_2^{17}O$ as a metabolite of the complex on the proton the $T_2$-weighted image. $T_1$-weighted images did not show any changes in the proton image intensities as compared to the $T_1$ control image. It was therefore evident from the data obtained, that on administration of the complex of the present invention to the target site, in vivo detection of the $H_2^{17}O$ tissue metabolite as one of the metabolized by products is certainly demonstrable by proton NMR imaging.

Although the invention has been illustrated by the preceding example, it is not to be construed as being limited to the materials employed therein, but rather, the invention is directed to the generic area as herein before disclosed. Various modifications and embodiments can be made without departing from the spirit or scope thereof.

What is claimed is:

1. A method for the non-invasive and visual estimation of the spacial distribution of $H_2^{17}O$ in the tissue of a subject, said method comprising administering to said subject an effective imaging amount of a diagnostic imaging agent comprised of a complex of oxygen-17 and a biologically acceptable liquid carrier, and wherein said complex has an ionic composition essentially equal to that of blood, and an average particle size of less than about 0.6 microns, and measuring the production of $H_2^{17}O$ in said tissue by means of a proton magnetic resonance imaging system.

2. The method of claim 1 wherein said agent is administered to said subject by infusion into the subject's blood stream by means of a catheter.

3. The method of claim 1 wherein said liquid carrier is a perfluorinated compound.

4. The method of claim 1 wherein said liquid carrier is perfluorotributylamine.

5. The method of claim 1 wherein said imaging agent is comprised of a biologically acceptable perfluorinated compound and an emulsifying agent in a volume ratio of compound to emulsifying agent of at least about 4:1, and oxygen-17 in a volume ratio of compound to oxygen-17 of up to 5:1; said diagnostic agent having an average particle size of less than about 0.6 microns.

6. A method for the non-invasive and visual estimation of the spacial distribution of $H_2^{17}O$ in the tissue of a subject said method comprising administering to said subject an effective imaging amount of oxygen-17 and monitoring the in vivo production of $H_2^{17}O$ by means of a proton magnetic resonance imaging system.

7. The method of claim 6 wherein said oxygen-17 is administered to said subject by infusion into the subject's blood stream by means of a catheter.

8. A method for preparing a diagnostic imaging agent useful in conjunction with a magnetic resonance imaging system for the imaging of spacial oxygen distribution in the biological tissue of a subject, said agent comprised of a biologically acceptable perfluorinated compound and a biological emulsifying agent in a volume ratio of compound to emulsifying agent of at least about 4:1, and oxygen-17 in a volume ratio of compound to oxygen-17 of up to 5:1; said diagnostic agent having an average particle size of less than about 0.6 microns, said method comprising the steps of:

(1) deoxygenating an emulsion of:
  (a) a biologically acceptable liquid, perfluorinated compound having an average particle size of less than about 0.6 microns, and (b) a biologically acceptable emulsifying agent, by at least one freeze-thaw cycle followed by sparging said emulsion with an inert oxygen-free gas;

(2) introducing oxygen-17 into the emulsion, and (3) thereafter recovering the diagnostic imaging agent.

9. A method for preparing a diagnostic imaging agent for the imaging of spacial distribution of $H_2{}^{17}O$ in biological tissue, said agent comprised of a complex of oxygen-17 and a biologically acceptable liquid carrier, and wherein said complex has an ionic composition essentially equal to that of blood, and an average particle size of less than about 0.6 microns, which comprises the steps of:

(1) deoxygenating an emulsion of:

(a) a biologically acceptable liquid, perfluorinated compound having an average particle size of less than about 0.6 microns, and (b) a biologically acceptable emulsifying agent, by at least one freeze-thaw cycle followed by sparging said emulsion with an inert oxygen-free gas;

(2) introducing oxygen-17 into the emulsion, and (3) thereafter recovering the diagnostic imaging agent.

10. The method of claim 9 wherein said perfluorinated compound is a perfluorinated compound selected from the group consisting of perfluorotributylamine, perfluorobutyltetrahydrofuran, perfluoro-n-octane, perfluoropolyether, perfluorodecalin, perfluoromethyldecalin, perfluororcyclohexyldiethylamine, perfluoroisopentylpyran and perfluorodibutylmethylmethylamine.

11. The method of claim 9 wherein said perfluorinated compound is perfluorotributylamine.

12. The method of claim 9 wherein said emulsifying agent is a poloyl.

13. The method of claim 9 wherein said emulsifying agent is a polyoxyethylene-polyoxypropylene copolymer.

* * * * *